(12) United States Patent
Morshed et al.

(10) Patent No.: US 10,405,746 B2
(45) Date of Patent: Sep. 10, 2019

(54) WIRELESS ANALOG PASSIVE SENSORS

(71) Applicant: The University of Memphis Research Foundation, Memphis, TN (US)

(72) Inventors: Bashir I. Morshed, Germantown, TN (US); Sergi Consul-Pacareu, Memphis, TN (US)

(73) Assignee: The University of Memphis Research Foundation, Memphis, TN (US)

( * ) Notice: Subject to any disclaimer, the term of this patent is extended or adjusted under 35 U.S.C. 154(b) by 255 days.

(21) Appl. No.: 14/686,275

(22) Filed: Apr. 14, 2015

(65) Prior Publication Data

US 2015/0289763 A1 Oct. 15, 2015

Related U.S. Application Data

(60) Provisional application No. 61/979,223, filed on Apr. 14, 2014.

(51) Int. Cl.
| | |
|---|---|
| *H04Q 9/00* | (2006.01) |
| *G08C 17/02* | (2006.01) |
| *H04Q 9/14* | (2006.01) |
| *A61B 5/00* | (2006.01) |
| *A61B 5/01* | (2006.01) |
| *A61B 5/0402* | (2006.01) |
| *A61B 5/0476* | (2006.01) |
| *A61B 5/053* | (2006.01) |
| *A61B 5/1455* | (2006.01) |

(52) U.S. Cl.
CPC .......... *A61B 5/0015* (2013.01); *A61B 5/0006* (2013.01); *A61B 5/01* (2013.01); *A61B 5/0402* (2013.01); *A61B 5/0476* (2013.01); *A61B 5/0533* (2013.01); *A61B 5/14552* (2013.01); *A61B 2562/02* (2013.01)

(58) Field of Classification Search
CPC .................................................... A61B 5/0015
See application file for complete search history.

(56) References Cited

U.S. PATENT DOCUMENTS

| | | | | |
|---|---|---|---|---|
| 5,458,123 A | * | 10/1995 | Unger | A61B 5/0006 128/903 |
| 2002/0067269 A1 | * | 6/2002 | Cadell | A61B 5/0017 340/573.1 |
| 2006/0009817 A1 | * | 1/2006 | Tulkki | A61B 5/0002 607/60 |
| 2006/0066449 A1 | * | 3/2006 | Johnson | A61B 5/1113 340/539.12 |
| 2007/0247316 A1 | * | 10/2007 | Wildman | A61B 5/1113 340/572.4 |
| 2008/0119716 A1 | * | 5/2008 | Boric-Lubecke | A61B 5/0205 600/407 |

(Continued)

*Primary Examiner* — Joseph H Feild
*Assistant Examiner* — Pameshanand Mahase
(74) *Attorney, Agent, or Firm* — Wayne Edward Ramage; Baker Donelson

(57) ABSTRACT

In one embodiment, a method is disclosed in which an analog sensor receives an electromagnetic (EM) wave (e.g., a radio frequency signal) from an interrogation device. The sensor converts a biological measurement of a subject into an electrical resistance and modulates a response to reflect the incident signal based on the electrical resistance. The sensor then provides the response to the interrogation device that corresponds to the biological measurement.

8 Claims, 10 Drawing Sheets

(56) References Cited

U.S. PATENT DOCUMENTS

| | | | |
|---|---|---|---|
| 2008/0241077 A1* | 10/2008 | Eickmeier | A61K 9/0019 424/45 |
| 2011/0004276 A1* | 1/2011 | Blair | A61B 5/0002 607/60 |
| 2012/0146795 A1* | 6/2012 | Margon | G06F 19/3406 340/573.1 |
| 2012/0146796 A1* | 6/2012 | Margon | A61B 5/05 340/573.1 |

* cited by examiner

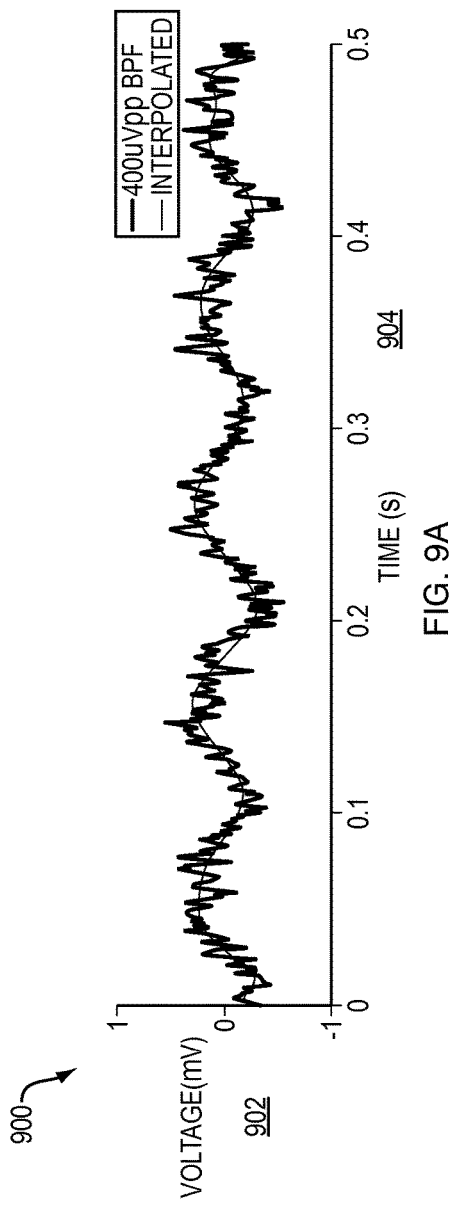
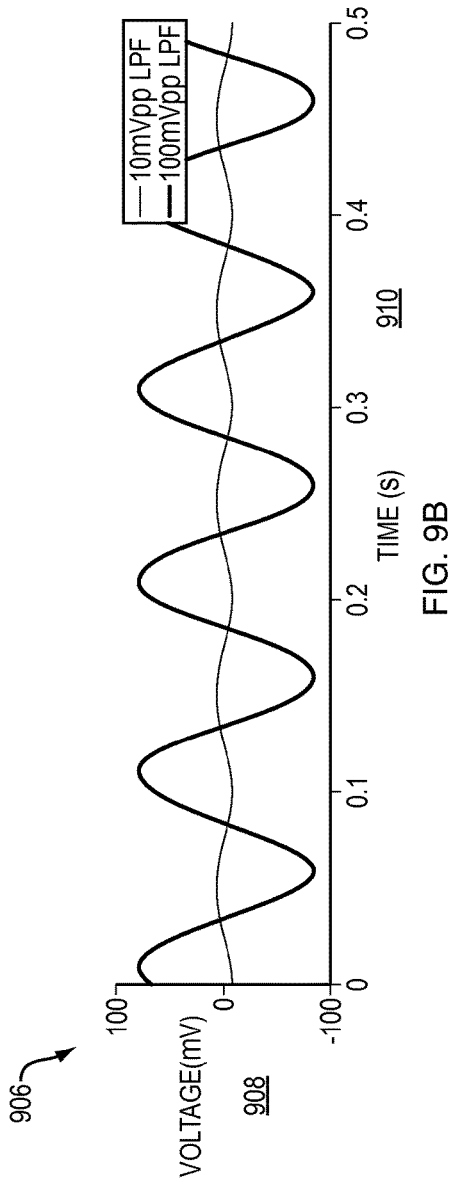

WIRELESS ANALOG PASSIVE SENSORS

CROSS REFERENCE TO RELATED APPLICATION

This application claims priority to and the benefit of U.S. Patent Application No. 61/979,223 filed in the United States Patent and Trademark Office Apr. 14, 2014, the entire contents of which are incorporated herein by reference.

TECHNICAL FIELD

The present disclosure relates generally to wireless sensors and, more particularly, to passive analog sensors, such as biosensors.

BACKGROUND

In general, diagnostics in a medical or clinical setting can be aided by determining as much information about a subject as possible. For example, an increase in a patient's body temperature is often a sign of illness or infection. In another example, a pulse oximetry measurement from the patent may be used to diagnose heart defects, sleep apnea, or measure the effects of sedation.

To facilitate measuring the condition of a subject, electronic sensors may be used. In recent years, an emerging area of research has been devoted to passive sensors that can be worn by a subject. Similar to radio frequency identification (RFID) tags, these sensors are passive in the sense that they may be powered in whole or in part by an external source. In many cases, a digital circuit is also used in the sensor for data acquisition by sampling measurements taken from the subject. This approach requires the active circuitry in the passive sensor to be activated by energy harvesting from the received electromagnetic (EM) energy, then retransmit sampled data or digital ID/code to the transmitter. This classical approach requires complex circuitry in the passive sensors, thereby increasing the cost of the sensor and requiring a greater amount of wireless power to be used to power the sensor.

Previous attempts to develop an analog passive sensor have concentrated primarily on capacitive measurements (e.g., using a varactor) that alter the tuned frequency of the passive sensor. These systems can be attached over a surface acoustic wave (SAW) substrate to provide different delays for different sensors, giving a Time Domain Multiplex capability. However, the use of a capacitive transducer also limits the types of sensing techniques that may be used by the sensor. In addition, the frequency response of a capacitive analog sensor shifts with the capacitance, thereby requiring the sensor to use a larger bandwidth. This limits the number of sensors that can be interrogated within a given bandwidth.

For the reasons stated above, existing passive biosensor techniques exhibit relatively poor performance and have not seen widespread adoption. Accordingly, there is a demand for alternative approaches to developing a passive biosensor that may be worn by a subject.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

In one embodiment, a method is disclosed in which an analog sensor receives an electromagnetic (EM) wave from an interrogation device. The passive sensor converts a biological measurement of a physiological parameter of the subject into an electrical resistance and modulates a response to the incident signal based on the electrical resistance. The modulated signal is analyzed by the interrogator to sense the change of the electrical resistances, thus detect changes of the corresponding biological signals. The passive sensor thus provides the response to the interrogation device.

In another embodiment, a method is disclosed in which an analog passive sensor receives a signal from an interrogation device. The sensor converts a biological measurement of a subject into an electrical resistance and modulates amplitude of a response to the RF signal based on the electrical resistance, hereby allowing measurement of the biological signal. The sensor then provides a backscattered response to the interrogation device that allows identification of corresponding biological signals.

In another embodiment, a method is disclosed in which an interrogation device generates an electromagnetic (EM) wave signal. The interrogation device provides the signal to a passive analog sensor that converts a biological measurement of a subject into an electrical resistance. The interrogation device also receives a response to the signal from the sensor that is based on the converted resistance. The interrogation device further analyzes the response to determine the biological measurement.

In another embodiment, a method is disclosed in which an interrogation device generates an electromagnetic (EM) wave signal. The interrogation device provides the signal to a passive analog sensor that converts a biological measurement of a subject into electrical reactance or impedance. The interrogation device also receives a response to the signal from the sensor. The sensor can be tuned at a resonant frequency. The interrogation device further analyzes the response to determine the biological measurement.

In another embodiment, a method is disclosed in which one or more interrogation devices generate multiple interrogation signals. The interrogation devices provide the interrogation signals to one or more passive analog sensors that are uniquely tuned to a single frequency. Each sensor converts one biological measurement of a subject into corresponding electrical resistance, reactance or impedance. The interrogation device(s) then receives the backscattered responses from these passive sensors simultaneously in a frequency-multiplexed or time-multiplexed or both formats. The interrogation device(s) further analyzes the responses to determine the biological measurements uniquely for each passive sensor.

In a further embodiment, a system is disclosed. The system includes an interrogation apparatus that generates an electromagnetic (EM) signal. The system also includes an analog sensor that receives the EM signal from the interrogation device, converts a biological measurement of a subject into an electrical resistance, modulates a response to the EM signal based on the electrical resistance, and provides the response to the interrogation device.

BRIEF DESCRIPTION OF THE DRAWINGS

The embodiments herein may be better understood by referring to the following description in conjunction with the accompanying drawings in which like reference numerals indicate identically or functionally similar elements, of which:

FIGS. 9A-9B illustrate example amplitude modulated signals received by an interrogator.

Figure 1:
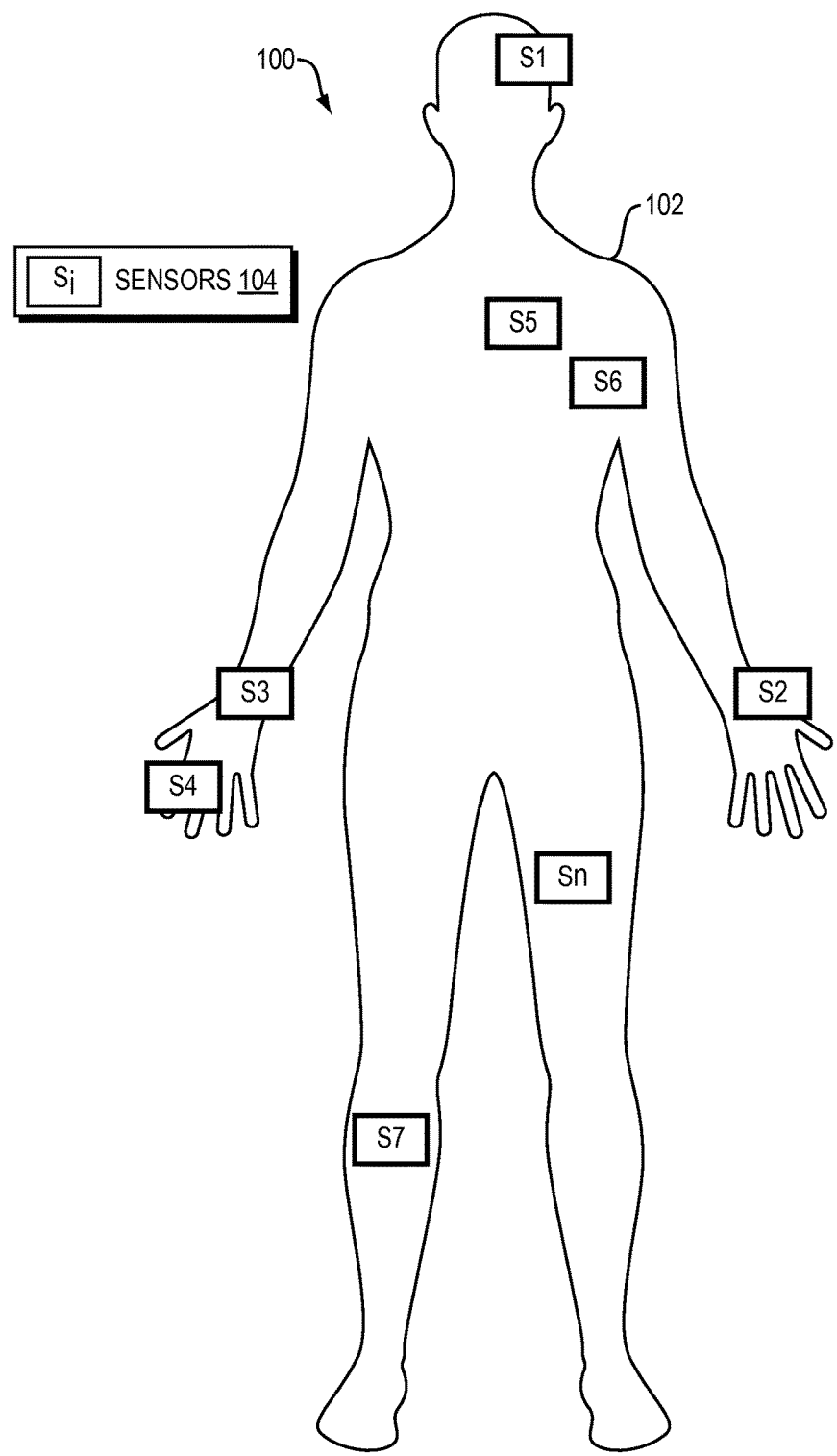
FIG. 1 illustrates an example passive biosensor system.

In the figures, reference numbers refer to the same or equivalent parts of the present invention throughout the several figures of the drawing.

DETAILED DESCRIPTION

To facilitate an understanding of the present invention, a number of terms and phrases are defined below. As used herein, the singular forms "a", "an", and "the" include plural forms unless the context clearly dictates otherwise. Thus, for example, reference to "a signal" includes reference to more than one signal.

Unless specifically stated, or obvious from context, as used herein, the term "or" is understood to be inclusive.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "subject" is meant to refer to an animal, preferably a mammal including a non-primate (e.g., a cow, pig, horse, cat, dog, rat, mouse, etc.) and a primate (e.g., a monkey, such as a cynomolgous monkey, and a human), and more preferably a human. In a preferred embodiment, the subject is a human.

Referring now to FIG. 1, an example biosensor system is shown, according to various embodiments. As shown, sensor system 100 may include any number of sensors 104 (e.g., sensors $S_1$ to $S_n$) that may be worn by, or implanted into, a subject 102. During operation, sensors 104 measure any number of different biosignals from subject 102. In other words, sensors 104 may convert measured biological responses from subject 102 into values represented as an electrical property (e.g., a current, voltage, resistance, capacitance, inductance, impedance, etc.). For example, the body temperature of subject 102 may be measured by one of sensors 104 using a thermistor that converts the measured temperature into an electrical resistance. Thus, a change in the resistance and electrical response of the sensor indicates a corresponding change in the body temperature of subject 102.

Sensors 104 may measure one or more types of biosignals from subject 102. For example, sensors 104 may take any or all of the following biological measurements from subject 102: a temperature measurement, a pulse measurement, a galvanic skin response measurement, a pulse oximetry measurement, an electrocardiography measurement, an electroencephalography measurement, combinations thereof, or the like.

During operation, an interrogator device queries sensors 104 for their respective biosignal measurements. The interrogator may do so by transmitting one or more signals to sensors 104 and, in response, receiving the measured biosignals from sensors 104. In one embodiment, an interrogation signal from the interrogator is sent using subject 102 as the medium. In other words, the signal from the interrogator and the response signal from a sensor 104 pass through subject 102. For example, a medical practitioner may use the interrogator to query a pulse oximeter sensor 104 (e.g., sensor $S_4$) located on a finger of subject 102 by touching the interrogator to the subject's stomach. When the subject is used as a communication medium between the interrogator and sensors 104, the interrogation signal sent by the interrogator may be selected to be below a safe exposure threshold for the corresponding EM or RF signal (e.g., based on signal strength, frequency, etc.). In another embodiment, air may be used in whole or in part as the communication medium between the interrogator and any of sensors 104. The sensors 104 can be tuned uniquely to different resonant frequencies for simultaneous frequency multiplexed sensing by the interrogator.

Figure 2:
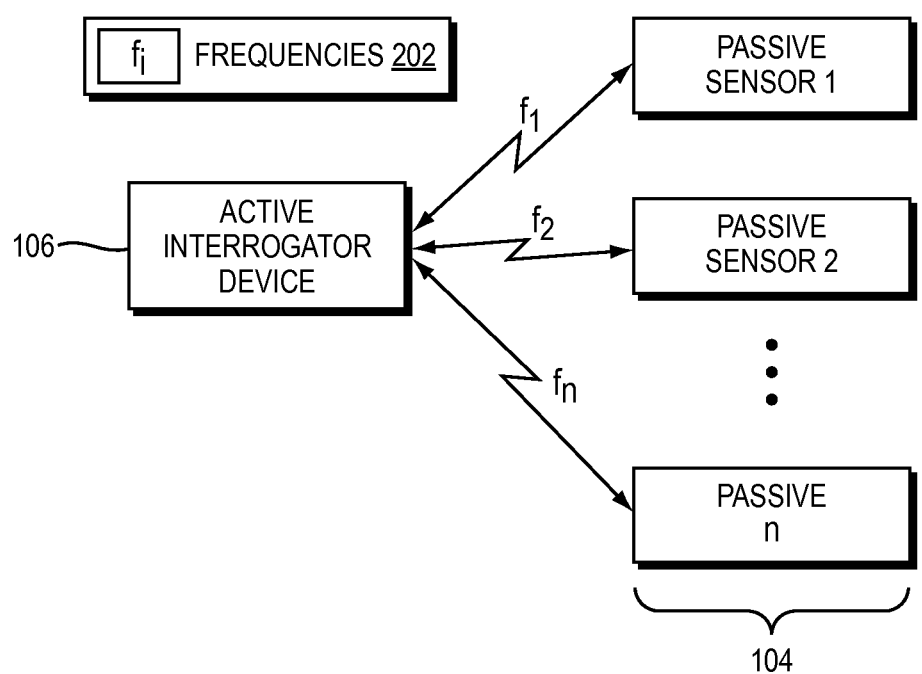
FIG. 2 illustrates an example of the system of FIG. 1 being interrogated.

Referring now to FIG. 2, an example of the interrogation of sensors 104 from FIG. 1 by an interrogator 106 is shown, according to various embodiments. As shown, interrogator 106 may query any number of sensors 104 attached to subject 102 by transmitting radio frequency (RF) or, more generally, electromagnetic (EM) signals to sensors 104. In one embodiment, each of sensors 104 may have its own interrogation frequency 202. For example, a first sensor 104 may be queried using a first frequency 202 (e.g., frequency $f_1$), a second sensor 104 may be queried using a second frequency 202 (e.g., frequency $f_2$), etc. In other words, the frequencies 202 used in sensor system 100 may be multiplexed by interrogator 106, thereby allowing any number of sensors 104 to be queried at the same time by interrogator 106.

In response to receiving a measurement request from interrogator 106 via an RF or EM signal, a corresponding sensor 104 returns an EM or RF signal via backscattering to interrogator 106 that indicates the biosignal measurement from subject 102. For example, the signal returned to interrogator 106 from a passive sensor with resistive temperature sensing element may have electrical characteristics, such as variation of backscattered signal that correlates with the variation of the resistance, that identify the measured or variation of body temperature of subject 102. Interrogator 106 may then convert the electrical characteristics of the returned signal into the value of the measured biosignal and provide the value to a user interface (e.g., an electronic display, a speaker, a printer, etc.). To facilitate the conversion of a received measurement from a sensor 104 into a value for use by a human operator, interrogator 106 may include, or be coupled to, any number of computing elements. For example, interrogator 106 may include, or be coupled to, one or more processors that are in communication with one or more memory devices (e.g., persistent or temporary data storage devices). The memory devices may also store program instructions that, when executed by the one or more processors, cause the processors to perform the operations described herein. For example, interrogator 106 may receive an analog signal from one of sensors 104, convert the received signal into digital form (e.g., using an analog to digital converter), analyze a representation of the signal using software to determine a measurement value, and provide the measurement value to a display.

According to various embodiments, sensors 104 are passive sensors that are interrogated by an active interrogator 106. In other words, sensors 104 may be activated in full or in part by consuming part of the incident energy while reflecting the remaining to the interrogator 106. The amount of energy consumed and reflected are dependent on resistive element which vary according to the biosignal measurement from subject 102, and thus a measurement can be made by the interrogator 106. Thus, sensors 104 may not require the use of an on-board power source, such as a battery, as well as do not require harvesting energy from the interrogation signals from interrogator 106. Conversely, interrogator 106 may be an active device that is powered by a battery, power supply, solar cell, or any other power source.

In one embodiment, a given sensor 104 includes a transducer that converts a measured biosignal into a corresponding electrical resistance. When receiving an interrogation signal from interrogator 106, a particular sensor 104 may modulate its response signal based on the resistance that results from the biosignal measurement. In a manner somewhat similar to radar, the response signal from the sensor 104 is effectively a backscatter of the interrogation signal. Interrogator 106 may then determine the corresponding value of the biosignal measurement, based on the modulation of the returned signal, which depends on the resistance of sensor 104.

Figure 3A:
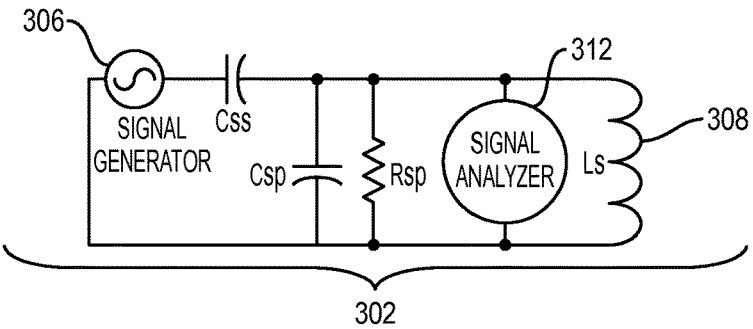
FIGS. 3A-3E illustrate example circuit diagrams for passive analog sensor systems.
Figure 3B:
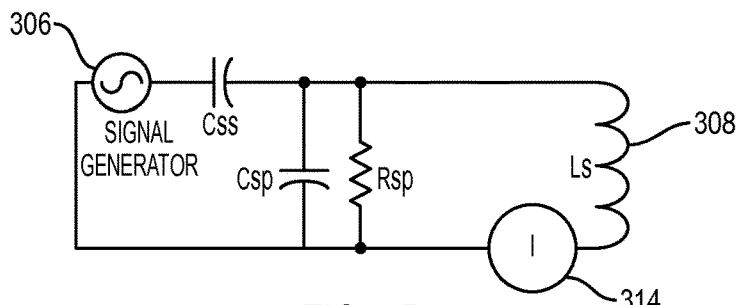

Referring now to FIGS. 3A-3B, example circuit diagrams for passive analog sensor systems are shown, according to various embodiments. Both of systems were used as simplified prototypes to demonstrate the potential mechanisms of operation and may be adapted for specific applications by one skilled in the art without deviating from the spirit of the teachings herein.

Figure 3C:
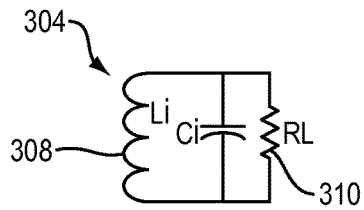

In FIG. 3A and FIG. 3C, sensor system includes an interrogator 302 (shown in FIG. 3A) and a single sensor 304 (shown in FIG. 3C). Interrogator 302 includes a signal generator 306 that generates an oscillated RF signal used to interrogate sensor 304. As shown, interrogator 302 and sensor 304 include inductors 308 (e.g., Ls in interrogator 302 and Li in sensor 304) that become inductively coupled when signal generator 306 is active. In response to the inductive coupling, an induced current becomes present in sensor 304, thereby activating the sensor. Modulation of the returned signal from sensor 304 back to interrogator 302 is based on the amount of resistance provided by a resistive load 310. A spectrum (or signal) analyzer 312 present in interrogator 302 is then used to analyze the signal returned from sensor 304, to obtain the biological measurement made by sensor 304. These elements of the interrogator system are only for illustration, and can be substituted with a number of techniques including but not limited to ASIC devices, SOC devices, COTS devices, prototyping boards, or many other existing or new technologies that are inclusive in this invention disclosure.

Figure 3D:
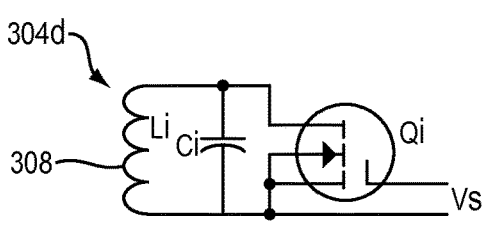
Figure 3E:
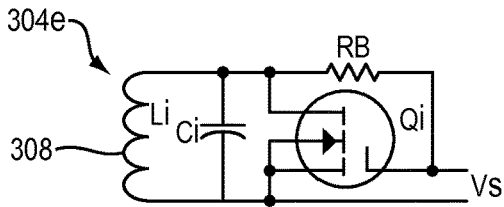

In FIG. 3B, biosensor system includes an inductor 314 and the sensor 304 (as shown in FIG. 3C). The configuration of FIG. 3B uses an inductor 314, instead of a signal analyzer 312 as shown in FIG. 3A, to thus sense amplitude modulation by measuring a current, as opposed to a voltage as shown in FIG. 3A. FIGS. 3D-3E illustrate alternate biosensor embodiments. As shown, sensors 304d and 304e may include metal oxide semiconductor field effect transistors (MOSFETs) that may be used to capture biopotentials (e.g., an ECG signal, an EMG signal, an EEG signal, etc.). The MOSFETs may be depletion type transistors (as shown) or, alternatively, may be enhancement type MOSFETs, in various embodiments. Notably, the characteristics of depletion-type MOSFETs (e.g., no biasing requirements, a default 'ON' state, a relatively linear ohmic region, etc.) may be used to convert a bipolar input voltage (Vs) into a resistance. However, enhancement-type MOSFETs with higher internal gains may be used in other embodiments to provide a higher sensitivity to Vs. Alternatively, a higher sensitivity may also be achieved by cascading multiple MOSFETs.

Additionally, the biosensor system in FIG. 3B may include a plurality of sensors 304 (e.g., a first through nth sensor). The interrogator 302 and sensors 304 may function in the same way as that of system shown in FIG. 3A but use different frequencies for each of sensors 304. For example, interrogator 302 may generate a first frequency (f1) to interrogate a first sensor 304, a second frequency (f2) to interrogate a second sensor 304, etc. Similarly, an inductor 314 may be configured in the sensor system of FIG. 3B having a plurality of sensors to distinguish between various sensors 304 based on the return frequencies used by the sensors. In one embodiment, the frequencies used in the system may correspond to the different sensor types of sensors 304. For example, frequency f1 may be used to query the subject's body temperature, frequency f2 to query the subject's pulse rate, etc.

As would be appreciated, the resistance of resistive load 310 may correspond to any measurement performed by sensor 304. For example, resistive load 310 may simply include a thermistor that converts temperature directly into a resistive load. In other cases, resistive load 310 may include a sensor component that performs a measurement using a different electrical property (e.g., a change in voltage, current, capacitance, etc.) and circuitry that converts the electrical property into the resistance of resistive load 310. In other embodiments, resistive load 310 may instead be a reactive or an impedance load. Accordingly, during operation, sensor system operates based on the principle that changes in the quality factor at the tuned frequency corresponding to measurements of the analog signals by sensor 304.

By varying the characteristics of the return signal from sensor 304 based on a change to its resistive load 310, sensor 304 may be constructed as an analog circuit. In other words, sampling circuitry is not needed in sensor 304 (e.g., to convert the biosignal or a related signal into digital form). Thus, sensor 304 may be smaller in construction, less complex in design, and potentially cheaper than a corresponding digital sensor. Additionally, the sensor 304 with the above described configuration may be used as a disposable or one-time use sensor. These sensors may be manufactured using a printing method or similar technique on materials such as thin film polymer, paper, fabric, etc.

Figure 4:
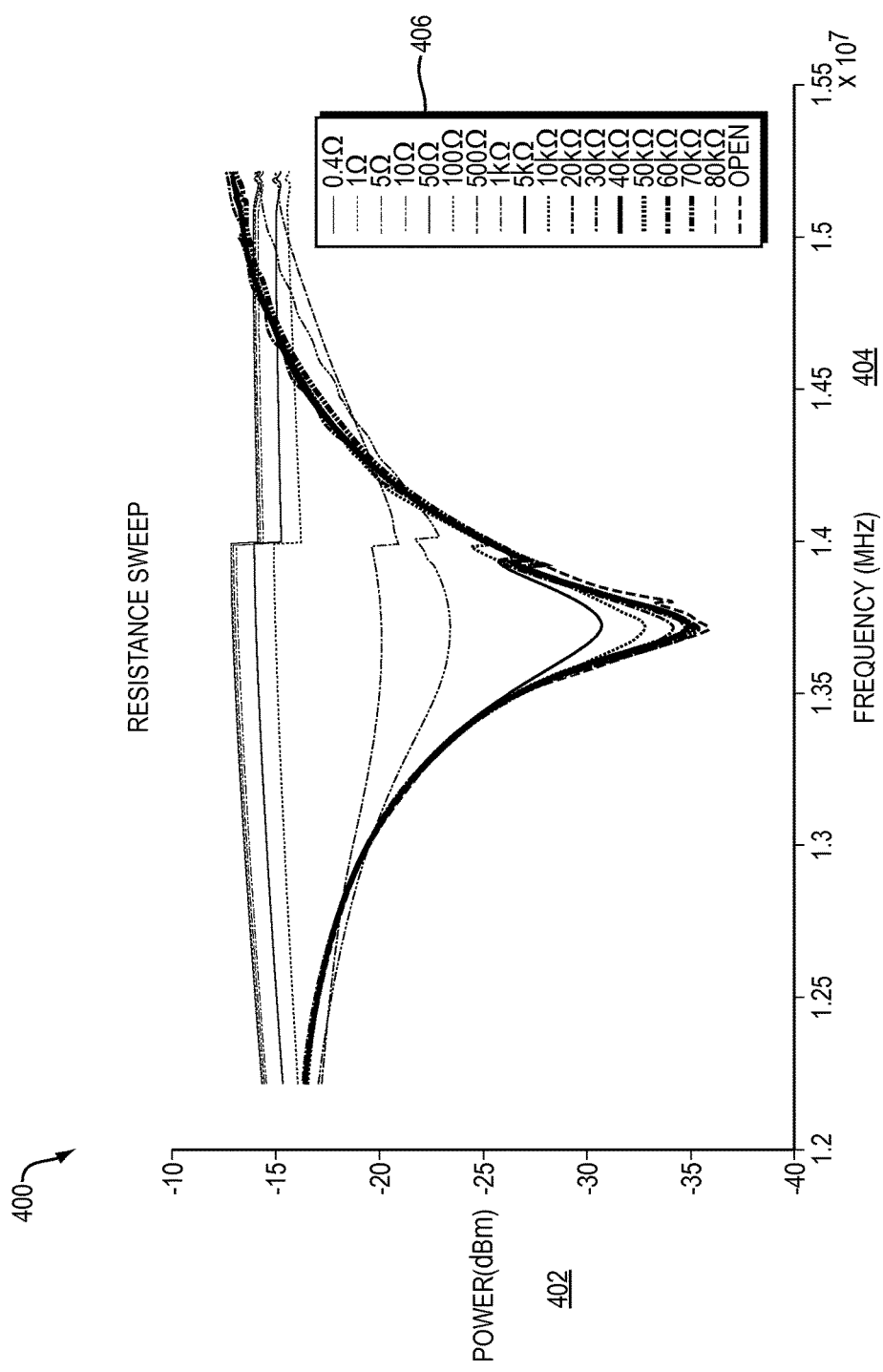
FIG. 4 illustrates an example plot of frequency responses for different resistive loads in a passive sensor system.

FIG. 4 illustrates an example plot 400 of frequency responses for different loads in a passive sensor system, according to various embodiments. As shown, the power 402 and frequency 404 responses of a test system in accordance with system 300 are plotted for different resistive loads 406. During testing, resistive loads varying from 0.4Ω to 80 kΩ were used in sensor 304. An interrogation signal of 13.754 MHz was then used to interrogate sensor 302 and the power and frequency responses of the returned signals recorded (e.g., via signal analyzer 312). As will be appreciated, other interrogation frequencies may be used by the interrogator. For example, radio frequencies may be selected from within an industrial, scientific, and medical (ISM) radio band, as defined by the International Telecommunication Union (ITU) or U.S. Federal Communications Commission (FCC), or any other possible signal in the EM spectrum.

As illustrated in plot 400, the signal response of the sensor varies with the resistive load used. Accordingly, variations in the resistance due to different values of the biosignal measured by the sensor result in corresponding variations in the characteristics of the signal returned from the sensor (e.g., from the mutual inductance formed between the interrogator and the sensor). Thus, during operation, the interrogator or a computing device coupled thereto may distinguish between the possible characteristics of the return signal to obtain the value of the biosignal measured by the sensor.

Figure 5:
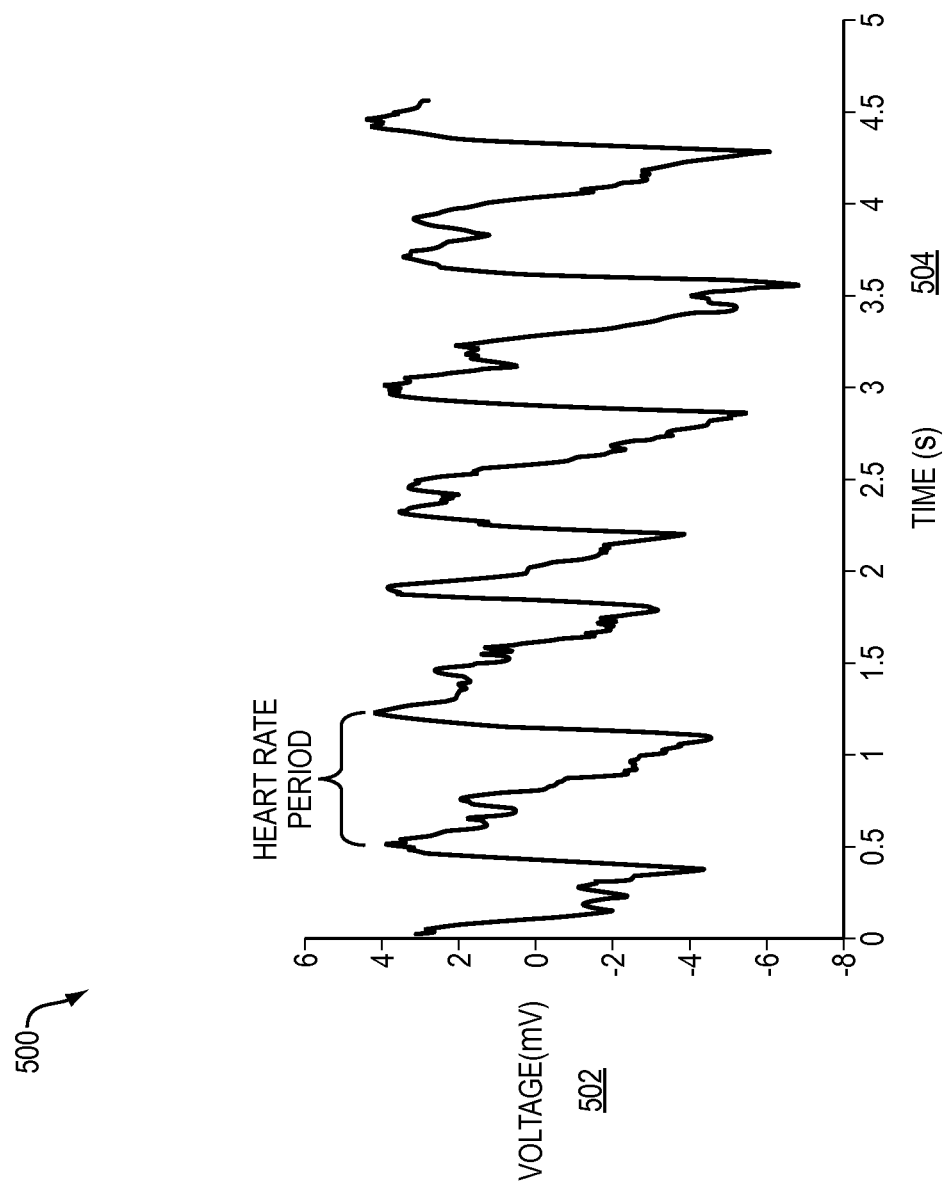
FIG. 5 illustrates test results for a passive heart rate sensor.

Referring now to FIG. 5, test results for a passive heart rate sensor are shown in plot 500, according to one embodiment. During testing, a pressure to resistance transducer was used for the resistive load of the sensor to transform the measured heart rate into a resistance. As will be appreciated, the heart rate of a subject may be detected as the change in mechanical pressure due to expansion of a vein during a heartbeat. In response to an interrogation signal from the interrogator, the variations in the resistive load of the sensor cause changes in the characteristics of the return signal. These changes were then translated into voltages 502. As shown in plot 500, change in the voltages 502 are plotted as a function of time 504. The pulse rate of the subject can thus be obtained by dividing the number of changes to voltage 502 within a given period of time. For example, as shown, the pulse rate of the subject is approximately 85 beats per minute, which was verified during testing using independent means.

Figure 6:
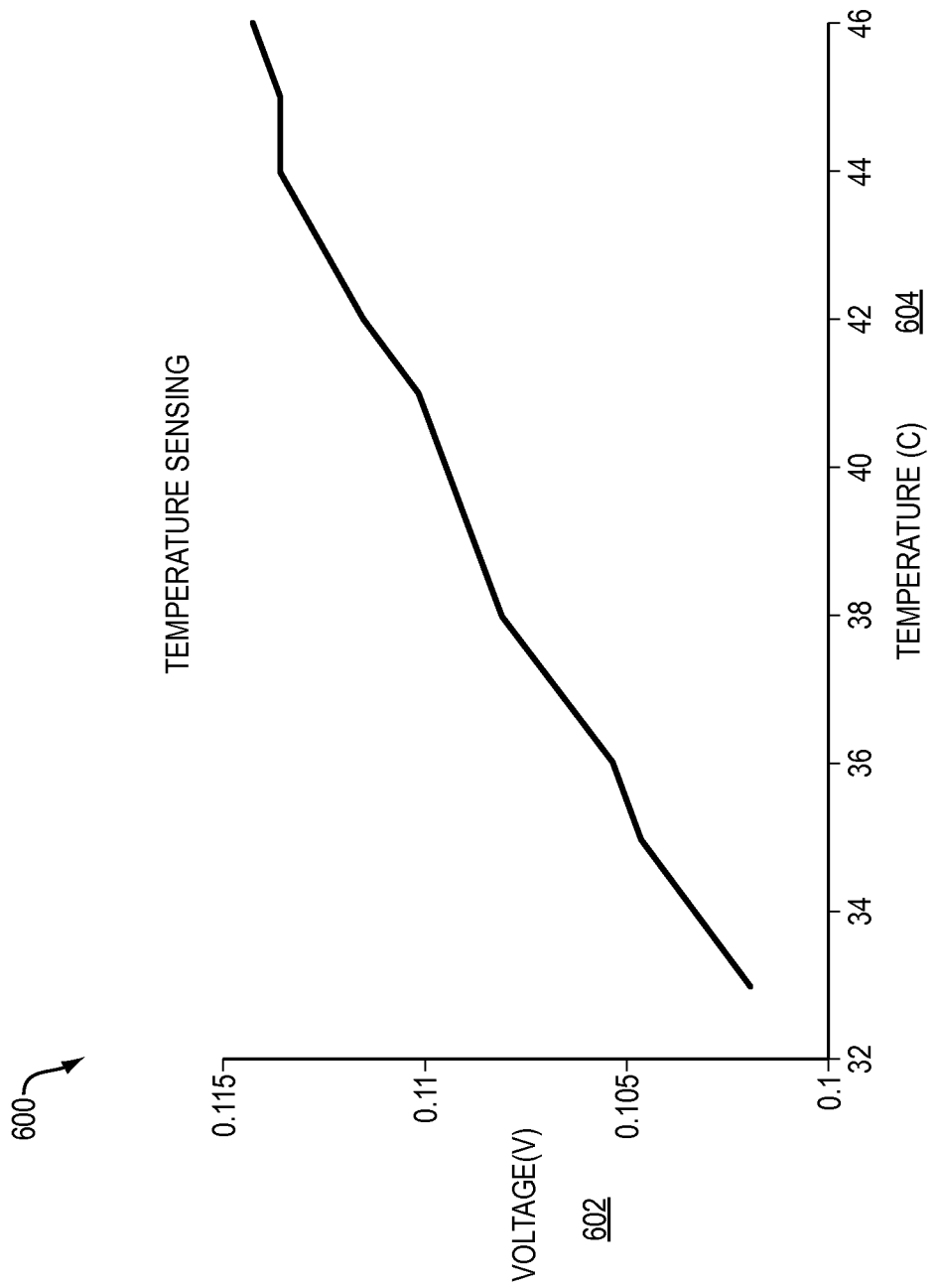
FIG. 6 illustrates test results for a passive thermometer.

Referring now to FIG. 6, test results for a passive heart rate sensor are shown in plot 600, according to one embodiment. During testing, a thermistor that converts a measured temperature into a corresponding resistance was used as the resistive load in the sensor. The resulting voltage 602 from the signal returned from the sensor to the interrogator is shown in plot 600 as a function of the temperature 604 applied to the thermistor. Accordingly, the body temperature of the subject can be obtained from the resulting voltage 602.

Figure 7:
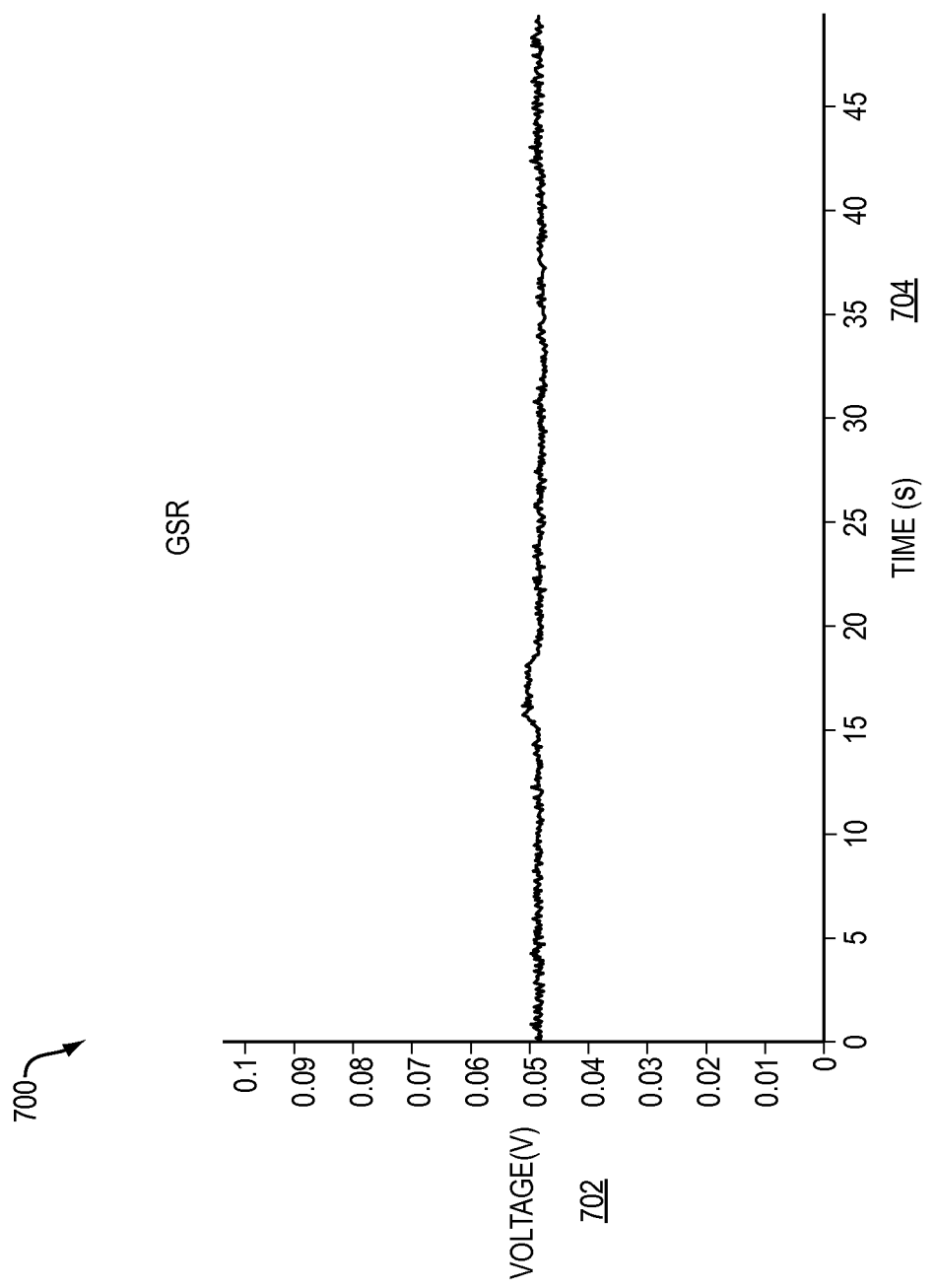
FIG. 7 illustrates test results for a passive galvanic skin response sensor.

Referring now to FIG. 7, test results for a passive galvanic skin response sensor are shown in plot 700, according to one embodiment. During testing, a pair of GS-26 electrodes (e.g., commercially available Ag/AgCl electrodes) were connected to two fingers of a subject in parallel with a 50 kΩ resistor and used as the resistive load of the passive sensor. The resistor was used to allow for proper measurement of the galvanic skin response which has a relatively high magnitude. Similar to plot 500, plot 700 shows a change in voltage 702 that resulted from the response signal sent by the sensor to the interrogator as a function of time 704. As would be appreciated, the voltage appearing in plot 700 is related to the galvanic skin response of the subject and can be used to obtain the value of the response.

Figure 8:
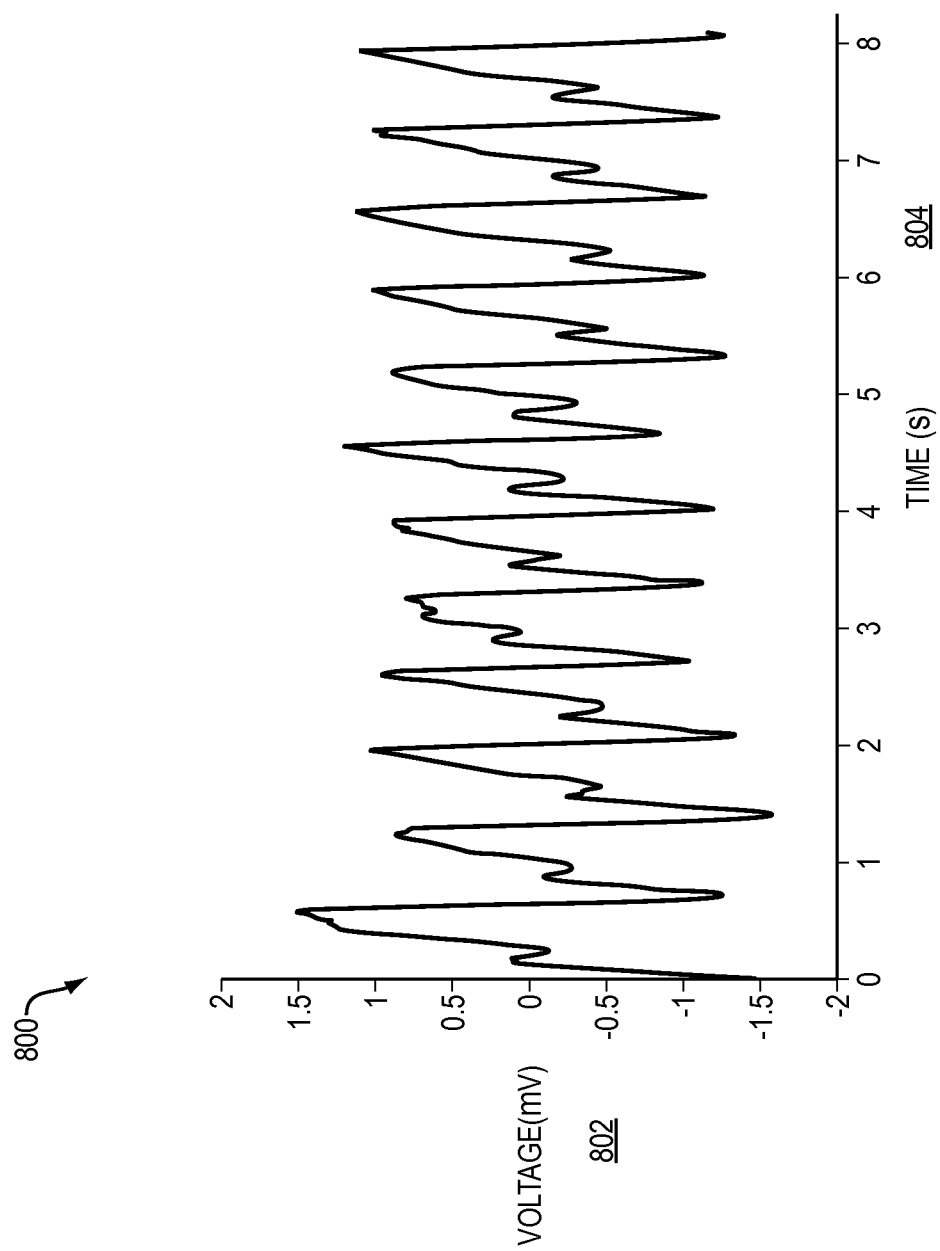
FIG. 8 illustrates test results for a passive pulse oximeter.

FIG. 8 illustrates test results for a passive pulse oximeter shown in plot 800, according to one embodiment. During testing, a light detecting resistor (LDR) was used for the resistive load of the passive sensor. Plot 800 depicts the change in voltage 802 that resulted from the response signal sent by the sensor to the interrogator as a function of time 804. By analyzing the voltage shown, the amount of oxygen saturation in the subject's blood can be determined.

FIGS. 9A-9B illustrate example amplitude modulated signals received by an interrogator, according to various embodiments. Referring now to FIG. 9A, this plot 900 shows a recorded waveform 902 (e.g., modulated load) of a sensor as a function of time 904. During testing, a sensor was used at a 20 mm distance between the interrogator and the sensor. In addition, a simulated biopotential of 400μ $V_{pp}$ (bandpass filter) was sensed at the sensor and is shown with an interpolated waveform within the range of the measured data points. Referring now to FIG. 9B, this plot 906 shows a recorded waveform 908 (e.g., modulated load) of a sensor as a function of time 910. During testing, a sensor was used at a 20 mm distance between the interrogator and the sensor. The plot 906 shows a simulated biopotential of 100 m $V_{pp}$ (low pass filter) with a 10 m $V_{pp}$ (low pass filter) input at the sensor. The time-domain plots of FIGS. 9A-9B demonstrate the capture of potential remotely using the passive sensors. The technique described herein above may be used for various tests including electrocardiography (ECG/EKG), electromyography (EMG), electroencephalography (EEG), or neuronal activity.

Figure 10A:
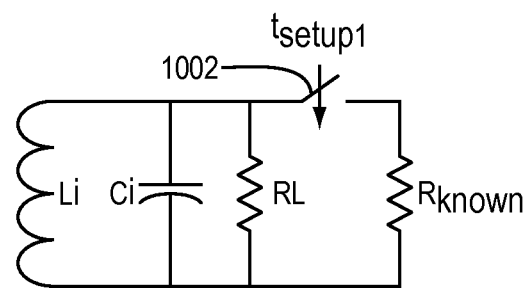
FIGS. 10A-10B illustrate example circuit diagrams used for calibration.
Figure 10B:
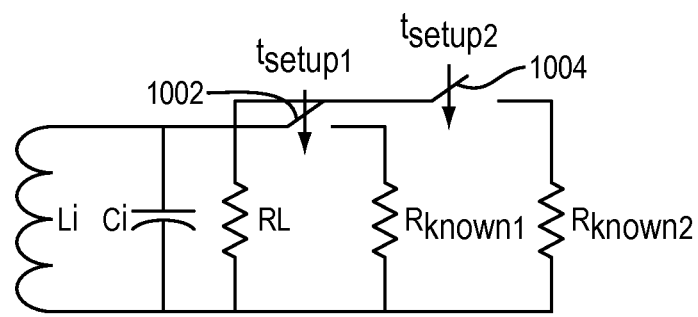

Referring now to FIGS. 10A and 10B, example circuit diagrams are shown to illustrate calibration methods according to various embodiments. FIG. 10A shows a sensor of the biosensor system that is to be attached to a subject. Upon attaching the sensor, to calibrate the system, a switch 1002 may be engaged (e.g., pressed) to short the known resistive load ($R_{known}$) in the circuit. The above described interrogator may then scan the frequency band to find the sensor with the $R_{known}$ and then may save the received power to calibrate the system. Since the sensor may be set using this described method, and the sensor is known by the interrogator to be of a particular type, the system may be calibrated based on a difference in the amplitude response.

FIG. 10B shows a sensor of the biosensor system in which two resistive loads are known. In particular, to calibrate the system once attached to the subject, the first switch 1002 may be engaged as described in relation to FIG. 10A to short the known first resistive load ($R_{known1}$). Then, a second switch 1004 may be engaged to short the known second resistive load ($R_{known2}$). The two known resistances allows the system to be calibrated for a known maximum and minimum value of the sensor RL based on a nominal value for the RL. Alternatively, a third switch (not shown) may be added to the circuit in series with the RL. Accordingly, the RL may be disconnected and the system may be calibrated using the two known resistive loads. In addition, two resistors (e.g., $R_{known1}$ and $R_{known2}$) may be used to encode the sensor type using the ratio of the resistances.

Furthermore, herein below two additional calibration methods will be described which may be executed independently or in combination with each other. The below calibration methods may be automatically performed without the input of a user. First, the system may be calibrated by adding a second coil and a second capacitor to the circuit which may be independent from the first capacitor which oscillates in the same frequency band, or medical (ISM) radio band, but at another frequency. The known frequency may have a known resistive load and thus the interrogator may use such known values to calibrate for frequency deviation and attenuation. Secondly, the system may be calibrated by rectifying the voltage and driving a MOSFET in series with a known resistive load ($R_{known}$). The known resistive load may be short-circuited in the coil when enough power is present in the coil, which may occur at start-up of the system to thus calibrate the system.

As will be appreciated, the above examples are intended only for the understanding of certain aspects of the techniques herein and are not limiting in nature. For example, the techniques herein may be adapted for use with any form of biosignal sensor by converting the sensed value into a corresponding resistive load for the passive sensor. In addition, while the techniques are described primarily with respect to a biosensor, it is to be appreciated that the techniques herein may be adapted for use with any other form of remote sensor in addition to those intended to be used with a biological subject (e.g., by measuring a non-biological system).

Advantageously, passive sensor techniques are disclosed that operate based on a sensed resistance/impedance change in a remote sensor. This allows for greater voltage sensitivity of the system allowing the support of a greater variety of supported sensor types. In addition, the techniques herein allow for a lowered bandwidth requirement, allowing for more sensors to be used simultaneously on a subject. Additionally, the techniques herein provide a simplified system design that is relatively compact and inexpensive.

The foregoing description has been directed to specific embodiments. It will be apparent, however, that other variations and modifications may be made to the described embodiments, with the attainment of some or all of their advantages. Accordingly this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A method, comprising:
    generating, by an interrogation device, a radio frequency (RF) wave signal used to activate a sensor;
    providing the RF signal to a passive analog sensor that converts a physiological measurement of a subject into an electrical resistance;
    receiving, at the interrogation device, a response to the RF wave signal from the sensor that is based on the converted resistance;
    analyzing the response of an analog modulation of a radio frequency signal amplitude to determine the physiological measurement;
    detecting, by the interrogation device, engagement of a switch to short a known resistive load;
    scanning, by the interrogation device, a frequency band to detect the sensor with the known resistive load; and
    storing, by the interrogation device, received power to calibrate the device and sensor for a difference in amplitude response.

2. The method as in claim 1, wherein the response is a backscattered signal of the RF wave signal at a tuned resonant frequency.

3. The method as in claim 1, further comprising:
    activating the passive analog sensor using the RF wave signal.

4. The method as in claim 1, further comprising:
    sending the RF wave signal as part of a frequency multiplexed signal; and
    using a different frequency of the frequency multiplexed signal to interrogate a second passive analog sensor.

5. The method as in claim 1, wherein the measurement comprises one or more of a temperature measurement, a pulse measurement, a galvanic skin response measurement, a pulse oximetry measurement, an electrocardiography measurement, or an electroencephalography measurement.

6. The method as in claim 1, further comprising:
    conveying the RF wave signal to the sensor using the subject as a medium.

7. The method as in claim 1, further comprising:
    conveying the RF wave signal to the sensor using air as a medium.

8. The method as in claim 1, wherein the RF wave signal is within an industrial, scientific, and medical (ISM) radio band.

* * * * *